United States Patent [19]

Winston et al.

[11] Patent Number: 4,851,212

[45] Date of Patent: * Jul. 25, 1989

[54] AIR DEODORIZER COMPOSITION AND METHOD

[75] Inventors: Anthony E. Winston, East Brunswick; Raymond S. Brown, Bridgewater; Frederick W. Lawson, Somerset; Norman Usen, Marlboro, all of N.J.

[73] Assignee: Church & Dwight Co. Inc., Princeton, N.J.

[*] Notice: The portion of the term of this patent subsequent to Apr. 26, 2005 has been disclaimed.

[21] Appl. No.: 137,197

[22] Filed: Dec. 23, 1987

Related U.S. Application Data

[63] Continuation of Ser. No. 820,694, Jan. 21, 1986, Pat. No. 4,740,366.

[51] Int. Cl.$^4$ ............................................... A61L 9/04
[52] U.S. Cl. ..................................................... 424/45
[58] Field of Search ......................................... 424/45

[56] References Cited

U.S. PATENT DOCUMENTS

| 2,959,225 | 11/1960 | Roberts | 166/147 |
| 3,317,372 | 5/1967 | Hart | 424/76.21 |
| 4,396,152 | 8/1983 | Alplanalp | 239/337 |
| 4,534,962 | 8/1985 | Marschner | 424/65 |
| 4,740,366 | 4/1988 | Winston et al. | 424/45 |

FOREIGN PATENT DOCUMENTS

| 0033668 | 6/1981 | European Pat. Off. . |
| 3347742 | 7/1985 | Fed. Rep. of Germany . |
| 1172183 | 10/1958 | France . |
| 1341709 | 1/1980 | France . |
| 2473315 | 7/1981 | France . |
| 1476117 | 6/1977 | United Kingdom . |

OTHER PUBLICATIONS

Chemical Abstracts 104:39534t (1985).
"Technical Aspects of Cosmetic/Personal Care and Food Aerosols", an article by Montfort A. Johnson (5/20–22, 1985).
The Aerosol Handbook, Montfort A. Johnson 2nd Ed. 1982, Wayne Dorland Co., pp. 177–178.
"Suspensions (Pressurized Powders)", Article by Raymond Brown, (5/20–22, 1985).
"Air Fresheners", a paper presented at the Inst. for Applied Pharmaceutical Sciences, (May 20–22, 1985).

Primary Examiner—Douglas W. Robinson
Assistant Examiner—Roger Gobrogge
Attorney, Agent, or Firm—Bryan, Cave, McPheeters & McRoberts

[57] ABSTRACT

An air deodorizer, and a method for deodorizing rooms therewith, utilizing an aerosol of a solution containing from 2–25% by weight of non-toxic, non-oxidizing, deodorizing agent, said solution constituting liquid droplets having a weight average droplet size of less than 50 microns, more than 90% of said droplets having a size, by count, of less than 10 microns.

8 Claims, No Drawings

AIR DEODORIZER COMPOSITION AND METHOD

This is a continuation of U.S. application Ser. No. 820,694, filed Jan. 21, 1976 now U.S. Pat. No. 4,740,366.

TECHNICAL FIELD

This invention relates to an air deodorizer, and more particularly to an air deodorizer which comprises an aerosol of finely divided droplets of a solution of a non-toxic, non-oxidizing deodorizing agent.

BACKGROUND OF THE INVENTION

Various techniques have previously been proposed for deodorizing rooms or other large volumes. Among known deodorizing means are static deodorants, powdered carpet and room deodorizers, treated filters and aerosol sprays.

Static deodorants operate by releasing fragrances or other substances into the ambient environment. The fragrances serve merely to mask those odors which may be present. Such deodorizers have been found moderately effective for masking some odors, but their efficiency is limited by the ability of the deodorizing ingredients to diffuse throughout the space to be deodorized, and the extent to which the malodors or other air pollutants diffuse into contact with the static deodorants. Consequently, the volume to be deodorized has an obvious effect on the efficiency of static-type deodorizers. Moreover, since the deodorizing ingredients employed in such products are generally fragrances, they are incapable of absorbing or destroying the unpleasant odors sought to be eliminated.

Some static deodorizers have been developed which are capable of absorbing odors in limited volumes. Thus, boxes of baking soda-based, or activated charcoal-based, deodorants have been utilized to deodorize refrigerators. Absorption of odors by these products is facilitated by the relatively rapid mechanical circulation of air throughout the limited volume treated. Generally, however, rapid deodorization of the air in restricted volumes such as refrigerators or the like is unnecessary; accordingly, inefficiencies associated with static deodorizers are unimportant for this particular application.

Filters of various types, treated with deodorizing chemicals such as activated charcoal or baking soda, have also been employed to deodorize air and reduce air pollution levels. It is necessary, however, to use such filters in conjunction with circulating fans. Moreover, deodorizing filters are ineffective for deodorizing unless large volumes of air are flowed through the filters, as compared with the total volumes to be deodorized. In addition, such filters must be changed or re-treated when the deodorizing chemicals are spent. Thus, the use of deodorizing filters has generally been restricted to recirculating hood filters positioned above kitchen ranges. In these limited circumstances, filters are effective deodorizers, largely due to their proximity to the source of the malodor.

Still other forms of deodorizers are known. Among them are powdered carpet and room deodorizers. As in the case of static deodorizers, powdered deodorizers either release fragrances or contain absorbents such as baking soda, and thus depend on diffusion of the active deodorizing agent. Powdered carpet deodorizers are thus effective in masking or absorbing odors present in the carpets or rugs to which they are applied, but are less effective in eliminating odors already present in the air.

It is also known to dispense deodorizing ingredients into the air in the form of aerosol sprays, i.e., sprays of gaseous suspensions of liquid droplets of the deodorizers. The use of aerosols permits more effective deoderization because the particles or droplets containing the deodorizing ingredients may be distributed throughout the room or other volume to be deodorized. The application of aerosol sprays is not dependent upon the relatively slow molecular diffusion required by static or like deodorizers. However, currently available aerosol sprays are subject to other serious disadvantages. For example, most such products contain only fragrances which, as noted above, do not absorb, neutralize or destroy malodors but merely mask them by adding a more pleasant odor for a limited time.

Certain aerosol sprays are dispensed in the form of relatively large liquid droplets which dissolve odorant molecules from the atmosphere before dropping out of and thereby cleansing the air. This mechanism is at best a temporary remedy since after removal of the droplets from the atmosphere the malodors can be re-released. Moreover, many malodorous compounds are insoluble in the droplets and consequently cannot be removed from the air in this manner.

A room deodorizer has also been developed (Erase, Economics Laboratories) containing as the sole deodorizing ingredient less than about 1% of the oxidizing agent sodium chlorite. Oxidizing agents such as sodium chlorite are, however, only effective against readily oxidizable malodors. Moreover, the prolonged use of such an oxidizing agent, or the use of higher concentrations of oxidizing agents, may pose a potential safety hazard. This type of product thus has limited safety and efficacy.

Numerous types of aerosol disinfectant sprays are also known, and marketed, for use as room deodorizers. Such disinfectant sprays may contain anti-microbial agents intended to kill odor causing bacteria. Significantly, however, many odors are not the result of bacterial action. Moreover, disinfectant aerosols do not eliminate malodors already present in the atmosphere.

Accordingly, it is a principal object of the present invention to provide an improved deodorizer composition and method which effects rapid, safe and effective deodorizing of the atmosphere in rooms and other large spaces, and which is not subject to the disadvantages associated with previously known deodorizers. Other objects and advantages of the invention will be apparent from the following detailed description of preferred embodiments thereof.

DISCLOSURE OF THE INVENTION

The present invention involves an air deodorizer comprising an aerosol of a solution containing about 2-25% of a non-toxic, non-oxidizing deodorizing agent, the aerosol constituting liquid droplets having a weight average droplet size of less than 50 microns, and more than 90% of the droplets having a droplet size, by count, of less than 10 microns; and a method for deodorizing the atmosphere by dispensing such aerosol. Deodorizers prepared in accordance with the invention provide rapid, safe and effective deodorizing. Moreover, by dispensing the aerosol in the form of fine, virtually invisible droplets of the deodorizing agent solution, virtually no visible residue normally forms on the furniture or other surfaces within the room or other volume treated. In this manner, the air deodorizer of the invention may be used without the unsightly residues associated with previous dry powder aerosol deodorizers.

The non-toxic, non-oxidizing deodorizing agent incorporated in the air deodorizer of the invention may be any material which chemically reacts with or otherwise neutralizes malodors without adversely affecting the user or the environment. Such materials are desirably active, and may be utilized, in solutions at mild pH values, e.g., within the range of from about pH 4–10 or, preferably, pH 5–9. Suitable non-toxic, non-oxidizing deodorizing agents useful in the method and composition hereof include the alkali metal bicarbonates, carbonates, or borates; the mono-, di- or tri-alkali metal ortho-phosphates; the alkali metal salts of the tripolyphosphates, pyrophosphates or hexametaphosphates; or the alkali metal salts of various carboxylic acids, e.g., acetic acid, citric acid, lactic acid, or malic acid or mixtures thereof. While any of these alkaline, non-oxidizing deodorizing agents may be dissolved and aerosolized in accordance with this invention, it is presently preferred to so utilize sodium or potassium bicarbonate, either alone or in admixture with one another or with low levels of alkali metal carbonates, for reducing the level of acidic odorants and pollutants in the air.

The particular deodorizing agent and/or the proportions thereof may of course be varied, depending upon the particular malodors or pollutants to be treated, and the characteristics of the specific deodorizing agent. Hence, care must be taken when utilizing alkali metal carbonates in the formulation since such materials are strongly alkaline and tend to irritate the nose. Preferably, when the deodorizing agent comprises a bicarbonate or bicarbonate-containing mixture, the bicarbonate comprises about 5–20% of the deodorizer solution, and contains no more than about 2% alkali metal carbonate(s).

In accordance with a further feature of the invention it has been found that when an alkalie deodorizing agent, e.g., an alkali metal bicarbonate, carbonate and/or borate, is utilized for reaction with an acid-acting malodor, e.g., foot odor, sauerkraut or cheese odor, markedly improved deodorizing is obtained by incorporating a deodorizing enhancing agent in the deodorizer solution. The enhancing agent is a material which releases ammonia under the conditions at which the deodorizer is applied, e.g., in mild alkaline solutions at pH values of about 7–10. Materials so useful include ammonium hydroxide, ammonium bicarbonate, or an ammonium carbamate such as urea. The enhancing agent may be incorporated in the deodorizer solution in amounts up to about 20% by weight thereof, preferably in amounts sufficient to release ammonia into the solution in the proportion of from about 0.05 to 0.5%, preferably from 0.1 to 0.3% by weight thereof. Surprisingly, the addition of such materials to a deodorizer solution containing an alkaline deodorizing agent synergistically enhances the deodorizing characteristics thereof. (See, for example, the comparative results obtained against the propionic acid malodor as set forth in Table IV below.)

The air deodorizer of the present invention may also contain other malodor blockers, in amounts of up to about 5% by weight of the solution. Suitable malodor blockers such as the proprietary odor blockers marketed under the Veilex trademark by Bush, Booke and Allen Inc., the Malabate trademark by Albert Verly Inc., or the N-alkyl N-ethyl morpholinium ethyl sulfates may be utilized, in addition to others which will occur to those skilled in the art.

Anti-microbial agents may be incorporated in the deodorizer in an amount of up to about 2% by weight of the solution. Many anti-microbial agents suitable for such use are known. Among those which may be incorporated in the aerosolized solutions hereof are phenols, alkyl quaternary ammonium halides, such as the long chain silyl quaternary ammonium compounds disclosed in U.S. Pat. No. 4,394,378 and the references cited therein, or other materials known to those skilled in the art. As will be appreciated, incorporation of antimicrobial agents into the deodorizer solutions of the present invention expands the usefulness thereof, because the aerosolized solutions can thus be used to effectively reduce certain bacterial populations, in addition to eliminating malodors.

The deodorizer hereof may also contain a fragrance, in an amount of up to about 3% by weight of the solution. Various types of known fragrances are suitable for such use, including floral, herbal, and pine essences. Other known fragrances may be similarly employed.

The deodorizing agent, alone or in admixture with deodorizing enhancing agents, additional malodor blockers, anti-microbial agents, fragrances and/or other additives, is suitably dissolved in a non-toxic, vaporizable solvent which may be readily aerosolized. Water is conveniently so utilized, though aqueous mixtures with lower alkanols or other non-toxic, volatile solvents may similarly be employed.

The thus compounded deodorizing solution is dispensed as a liquid/gas aerosol. The aerosol may be produced in any desired manner, e.g., through an appropriate valve under the pressure of a liquefied, propellant, which is gaseous under normal ambient conditions, or by means of a suitable mechanical pump and aerator mechanism.

Preferably, the deodorizing solution is dispensed from an aerosol spray container under pressure of such a propellant in the form of liquid droplets dispersed in the propellant. Any conventional propellant, either alone or in admixture with other propellants, may be employed for this purpose. Materials so useful include normally gaseous hydrocarbons e.g., $C_2$–$C_5$ hydrocarbons such as propane, n-butane, or isobutane; volatile ethers such as dimethyl ether; conventional halogenated hydrocarbon propellants such as dichlorodifluoromethane, 1,2-dichloro-1,1,2,2-tetrafluoroethane, mixtures of dichlorodifluoromethane and trichloromonochloromethane or other "Freon" propellants; or the ecologically preferred halogenated hydrocarbon propellants chlorodifluoromethane, 1,1,-difluoroethane, 1,1-chlorodifluoroethane, or blends of two or more of these propellants with one another, with dimethyl ether or with normally gaseous hydrocarbons, marketed as the "Dymel" family of propellants. When such a propellant or propellant blend is utilized to disperse the deodorizing solution, and admixed therewith under pressure in an aerosol spray can, the propellant generally comprises between about 8 to 40% by weight of the resulting aerosol spray.

Whether produced under the pressure of a liquefied gaseous propellant or by mechanical pump means, the air deodorizer hereof is dispensed in the form of an aerosol having a fairly broad droplet size distribution range, the droplets having an average size, based on weight, of less than 50 microns, but more than 90% of the droplets having a size, by count, of less than 10 microns. The droplet size distribution range can be measured using any suitable particle size analyzer such as a Malvern ST1800 Particle Size Analyzer with a 300 mm lens. Average droplet size by count is measured by determining the average droplet diameter. Average droplet size by weight is measured by determining the average droplet weight and calculating the particle diameter of a droplet of this weight.

Preferably, no more than about 30% by weight of the dispersed phase droplets (the droplets of the deodorizing solution) has a size (i.e., maximum dimension) greater than 60 microns, no more than about 15% by weight of the droplets has a size greater than 80 microns, and no more than about 6% by weight of the droplets has a size greater than 100 microns. In fact, the majority of the droplets of the aerosol of the invention are in the invisible submicron size range, preferably more than 90% (by count) having a droplet size of less than 10 microns and more than 75% (by count) having a droplet size of less than 1 micron.

The above noted average droplet sizes based on weight are relatively high due to the presence of a few large size, heavy droplets. (Thus, the average droplet size based on weight of three 120 micron sized droplets and ninety-seven one micron sized droplets would be about 37 microns, whereas the average droplet size of such a mixture, based on count, would be about 4.6 microns.)

Conventional dry powder-containing aerosols may also possess weight average particle sizes of less than 50 microns (see Control L below). However, these powder aerosols incorporate substantially uniform size, larger particles than the liquid aerosols of the present invention. (Thus, in contrast to the present composition, the dry powder aerosol of Control L contained virtually no particles in the submicron range - see Table VI below.) Unlike the present composition, such dry powder-containing aerosols leave unacceptable residues on furniture or other substrates after use.

It is believed that the liquid aerosol composition of the invention does not, in normal use, leave any visible residue because the majority of the liquid droplet dispensed are in the submicron range. It may be shown, by application of Stokes Law, that when 50 micron particles having a specific gravity between about 0.8 and 1.2 are sprayed into uncirculated air they will remain suspended for from about 11 to 17 seconds, whereas comparable one micron sized particles will remain suspended for from about 8 to 12 hours. Since the atmosphere in a room may be exchanged several times within the course of a 24 hour period, it will be understood that aerosol droplets of the order of one micron or less dispensed in a room are virtually never deposited on any substrates therein. Accordingly, while a dry powder aerosol having a weight average particle size of, for example, 37 microns readily forms an unacceptable residue on furniture or the like, the liquid aerosol of the invention, constituted of droplets the majority of which are in the submicron range, forms no such residue.

The preceding is believed to explain the mode of operation of the aerosol deodorizer of the invention without, however, being intended to be limiting thereof. Rather, the scope of the invention is set forth in the claims appended hereto in the light of the foregoing general disclosure and the following detailed description of preferred embodiments of the compositions and methods hereof.

BEST MODE FOR CARRYING OUT THE INVENTION

Preferably, the air deodorizer of the present invention comprises an aerosol of an aqueous solution containing the following ingredients:

|  | % By Weight |
|---|---|
| DEODORIZING AGENT: | |
| Sodium Bicarbonate | 0 to 5 |
| in admixture with | |
| Potassium Bicarbonate | 2 to 20 |
| DEODORIZING ENHANCING AGENT: | |
| as released ammonia | 0.05 to 0.5 (preferably 0.1 to 0.3) |
| FRAGRANCE: | 0 to 50 |
| SOLVENT: | |
| Water | 95 to 70 |

The preferred compositions are prepared by compounding the aqueous solution, charging the solution into the aerosol container, adding the fragrance and/or other additives, and charging the liquefied propellant (preferably propane/isobutane mixes) under a pressure of from about 20 to 80 psig. Upon release of the resulting dispersion through an appropriate valve, e.g., a valve of the type described in U.S. Pat. No. 4,396,152, marketed as an "Aquasol" valve by Precision Valve Co., the solution is aerosolized in the form of minute liquid droplets as indicated hereinabove.

The following examples in which all parts and percentages are given by weight, illustrate particularly preferred embodiments of the air deodorizer and air deodorizing method hereof:

A.

Preparation Of Preferred Embodiments Of The Air Deodorizer Of The Invention

A number of aerosol formulations were prepared in accordance with the invention, incorporating sodium bicarbonate (Examples 1–4), sodium bicarbonate/potassium bicarbonate (Examples 5–7) or sodium bicarbonate/sodium carbonate (Examples 8–10) a deodorizing agent, as ammonium hydroxide (Examples 2,5 and 7), urea (Examples 3,6,9 and 10) or ammonium bicarbonate (Example 4) as a deodorizing enhancing agent, and glycerine (Examples 6 and 10) as an evaporation retarder, in aqueous solution. The respective formulations were then charged to an aerosol dispenser and liquefied. Propellant was added under a pressure of 55–70 psig. The dispenser was equipped with a valving mechanism such that each of the aerosols dispensed had an average droplet size of less than 50 microns by weight, more than 80% of the droplets being in the submicron range by count.

The compositions of the respective test aerosols are set forth in Table I below:

TABLE I

DEODORIZER AEROSOL FORMULATIONS OF THE INVENTION

| Ingredient (% by Wt.) | Ex. 1 | Ex. 2 | Ex. 3 | Ex. 4 | Ex. 5 | Ex. 6 | Ex. 7 | Ex. 8 | Ex. 9 | Ex. 10 |
|---|---|---|---|---|---|---|---|---|---|---|
| sodium bicarbonate | 5 | 5 | 5 | 5 | 2 | 1 | 2 | 5.0 | 5.0 | 5.0 |
| potassium bicarbonate | — | — | — | — | 10 | 10 | 10 | — | — | — |
| sodium carbonate | — | — | — | — | — | — | — | 5.0 | 5.0 | 2.0 |
| ammonium hydroxide (28%) | — | 0.5 | — | — | 0.5 | — | 0.5 | — | — | — |
| urea | — | — | 15 | — | — | 15 | — | — | 5.0 | 15.0 |
| ammonium bicarbonate | — | — | — | 3 | — | — | — | — | — | — |
| glycerine | — | — | — | — | — | 1 | — | — | — | 1.0 |
| fragrance | 0 | 0 | 0 | 0 | 0 | 0 | 1 | 0 | 0 | 0 |
| water | 95.5 | 94.5 | 80 | 92 | 87.5 | 73 | 86.5 | 90.0 | 85.0 | 77.0 |
| propellant | A | A | A | A | A | A | B | A | A | A |
| solution:propellant ratio | 65:35 | 65:35 | 65:35 | 65:35 | 86:14 | 80:20 | 86:14 | 80:20 | 80:20 | 80:20 |

Fragrances: Floral
Propellants: propane/isobutane mixtures to provide A = 55 psig  B = 70 psig

B.

Comparison of Malodor Reduction By The Deodorizer Of The Invention And Prior Commercial Products The efficacy of an aerosol deodorizer of the invention (Example 7 above) in destroying malodors was determined, and compared with currently available commercial deodorizers, employing the following test procedure:

Gutted refrigerators modified to eliminate the compressor cooling function but with the circulating fans left intact, were used as test chambers. The ports to the freezer sections were sealed off. In each test, an aerosolized malodor was introduced into the chamber via an injection port provided in the chamber door. The aerosol malodor was sprayed into the port for 2-10 seconds, depending on the malodor, and allowed to circulate throughout the chamber for a period of 10 minutes. The circulating fan operated during this period to insure thorough and even distribution of the malodor throughout the test chamber. The circulating fan continued to operate throughout the subsequent test period.

Upon completion of the 10 minute circulation period, an aliquot of the malodor was extracted from the chamber with a one liter syringe, via the injection port. The malodor level of the sample was determined and used as the initial control level. The test deodorizer was then injected into the test chamber for 6 seconds. Samples of the air within the chamber were extracted at various time periods, and the malodor levels measured. In each instance, the malodor level was determined subjectively by a 10-member sensory panel on a 0 to 15 continuous scale. Two different malodors were utilized in the experimental tests. First, a simulated "GSA Bathroom Odor" was produced employing an aerosolized dispersion of 0.5% of a malodor composition consisting of dipropylene glycol (63.82%), mercaptoacetic acid (21.18), n-caproic acid (6.0%), n-methylmorpholine (6.0%), p-cresyl isovalerate (2.18%), skatol (0.91%), and beta-thionaphthol (0.91%) in 99.5% dipropylene glycol. The resulting malodor concentrate was dispensed from an aerosol can using a liquefied blend of propane (25%) and i-butane (75%) in a 4:1 weight ratio of concentrate to propellant. The second malodor, simulating a "Smoke Odor," was produced by smoking one half of a Camel cigarette in a gallon jar, 500 cc, of the smoke being dispensed.

The percent malodor reduction and the relative fragrance levels were determined in each test, 1, 5, and 60 minutes after injection of the test deodorizer. The fragrance levels were determined on the same 0-15 scale used to evaluate the malodors, but in the presence of the respective malodors. The malodor and fragrance levels were also determined by the sensory panel for two control deodorizers, Control A, the Wizard "Summer Memories" deodorizer available from Boyle-Midway Co. and containing a floral fragrance and propellant; and Control B, the Glade "Early Spring" aerosol deodorizer available from S. C. Johnson & Co. and containing a floral fragrance emulsified in water.

The results obtained in the comparative tests are set forth in Table II below. It will be noted from the table that markedly superior odor reduction was obtained employing the aerosol deodorizer of the present invention as compared with the prior commercial deodorizers. It will also be noted that the fragrance levels observed by the test panel for the formulations of the invention were comparable to those observed for the control deodorizers, thus negating the possibility that the malodor reductions observed might have been attributable only to masking by the respective fragrances.

TABLE II

COMPARISON OF MALODOR REDUCTION PRODUCED BY AIR DEODORIZER OF THE INVENTION AND PRIOR COMMERCIAL AIR DEODORIZERS

| | % Malodor Reduction | | |
|---|---|---|---|
| | Ex. 7 | Control A "Summer Memories" | Control B "Early Spring" |
| 1 Minute After Deodorizer Injection | | | |
| "Bathroom Odor" | 54.9% | 39.0% | 49.6% |
| (Fragrance Level) | (5.9) | (6.0) | (4.9) |
| "Smoke Odor" | 42.8% | 19.8% | 15.3% |
| (Fragrance Level) | (5.5) | (5.7) | (3.5) |
| 5 Minutes After Deodorizer Injection | | | |
| "Bathroom Odor" | 54.4% | 39.5% | 27.8% |
| (Fragrance Level) | (4.6) | (5.9) | (4.5) |
| "Smoke Odor" | 52.3% | 22.2% | 18.6% |
| (Fragrance level) | (4.8) | (4.9) | (3.8) |
| 60 Minutes After Deodorizer Injection | | | |
| "Bathroom Odor" | 56.4% | 11.4% | 26.4% |
| (Fragrance Level) | (3.2) | (3.2) | (3.6) |
| "Smoke Odor" | 42.2% | 33.1% | 21.7% |
| (Fragrance Level) | (3.2) | (3.7) | (3.5) |

C.

Further Comparison of the Characteristics Of Deodorizers of the Invention Against Specific Malodors The aerosols of Examples 3,5,6 and 8–10 were tested against a number of different malodors, employing the test procedure described in Section B above. An aerosol of distilled water (80%) pressurized with a hydrocarbon propellant (25% propane, 75% i-butane to provide a pressure of 55 psig) was used as a control (Control C). The deodorizing effects were tested against the following malodors:

*Acetic acid:* 20% concentrate (90% distilled water and 10% acetic acid), and 80% of a 25% propane, 75% i-butane propellant (sprayed into a refrigerator for 2 seconds).

*Propionic acid:* 80% concentrate (90% distilled water and 10% propionic acid), and 20% of a 25% propane, 75% i-butane propellant (sprayed into a refrigerator for 3 seconds).

*Iso-Valeric acid:* 80% concentrate (98% distilled water and 2% valeric acid), and 20% of a 25% propane, 75% i-butane propellant (sprayed into a refrigerator for 3 seconds).

*Trimethylamine:* 80% concentrate (95% distilled water and 5% trimethylamine), and 20% of a 25% propane, 75% i-butane propellant (sprayed into a refrigerator for 3 seconds).

*"Garbage Odor"*: 80% compost extract and 20% of a 25% propane, 75% i-butane propellant (sprayed into a refrigerator for 10 seconds).

The compost extract was prepared by placing chicken, broccoli, grapefruit, oranges, lemons, potatoes, tomatoes, carrots, lettuce, corn, cabbage, asparagus, coffee grounds and tea bags in a plastic container, allowing them to decompose for one month at room temperature, placing the decomposed mixture in a blender with an equal amount of water, and filtering the same;

*"GSA Bathroom Odor"*-prepared as described in Section B, above (sprayed into a refrigerator for 3 seconds).

*"BBA Pet Odor"*-80% concentrate (0.5% pet malodor and 99.5% di-propylene glycol), and 20% of a 25% propane, 75% i-butane propellant (sprayed into a refrigerator for 2 seconds).

*"Cat Urine Odor"*-80% concentrate (5% filtered female cat urine and 95% distilled water), and 20% of a 25% propane, 75% i-butane propellant (sprayed into a refrigerator for 3 seconds).

The deodorizing effects obtained varying periods after introduction of the deodorizer formulations are given in Tables III A–E below, which summarize the results of different side-by-side comparative test:

TABLE IIIA
DEODORIZING EFFECTS AGAINST DIFFERENT MALODORS

| | % Malodor Reduction | | |
|---|---|---|---|
| 30 Seconds After Deodorizer Injection | Ex. 3 | Ex. 6 | Control C (Water) |
| Propionic Acid | 53 | 82 | 13% |
| Valeric Acid | 48 | 55 | 20% |
| 5 Minutes After Deodorizer Injection | Ex. 9 | Ex. 10 | Control C (Water) |
| Acetic Acid | 70% | 82 | 22% |
| Propionic Acid | 58% | 63% | 27% |

TABLE IIIB
DEODORIZING EFFECTS AGAINST DIFFERENT MALODORS

| | % Malodor Reduction | |
|---|---|---|
| 30 Seconds After Deodorizer Injection | Ex. 5 | Control C |
| Propionic Acid | 71.1% | 6.2% |
| Trimethylamine | 34.3% | 11.3% |
| "Garbage odor" | 42.9% | 15.9% |
| "GSA Bathroom odor" | 34.6% | 7.5% |
| "BBA Pet Odor" | 28.4% | 6.0% |
| "Cat Urine Odor" | 41.1% | 24.7% |
| 5 Minutes After Deodorizer Injection | Ex. 5 | Control C |
| Propionic Acid | 73.1% | 7.1% |
| Trimethylamine | 31.7% | 5.3% |
| "Garbage odor" | 40.4% | 7.0% |
| "GSA Bathroom odor" | 28.3% | 3.9% |
| "BBA Pet Odor" | 25.0% | 3.7% |
| "Cat Urine Odor" | 38.8% | 24.1% |

TABLE IIIC
DEODORIZING EFFECTS AGAINST DIFFERENT MALODORS

| | % Malodor Reduction | | | |
|---|---|---|---|---|
| | 1 Minute After Deodorizer Injection | | 5 Minutes After Deodorizer Injection | |
| | Ex. 8 | Control C | Ex. 8 | Control C |
| Acetic Acid | 59% | −24% (increased malodor) | 60% | 20% |
| Propionic Acid | 55% | 9% | 43% | 11% |

TABLE IIID
DEODORIZING EFFECTS AGAINST DIFFERENT MALODORS

| | % Malodor Reduction | | | |
|---|---|---|---|---|
| | 1 minute After Deodorizer Injection | | 5 minutes After Deodorizer Injection | |
| | Ex. 9 | Control C | Ex. 9 | Control C |
| Propionic Acid | 61% | 18% | 77% | 11% |

TABLE IIIE
DEODORIZING EFFECTS AGAINST DIFFERENT MALODORS

| | % Malodor Reduction | | | |
|---|---|---|---|---|
| | 1 Minute After Deodorizer Injection | | 5 Minutes After Deodorizer Injection | |
| | Ex. 10 | Control C | Ex. 10 | Control C |
| Propionic Acid | 66% | 18% | 76% | 22% |
| Valeric Acid | 47% | 28% | 62% | 21% |

D.

Effect Of The Addition Of Deodorizing Enhancing Agents

The effect of the respective deodorizing enhancing agents is illustrated by comparison of the deodorizing characteristics of the aerosol formulations of Examples 1–4 above. As indicated above, the aerosol of Example 1 contained sodium bicarbonate without any enhancing agent, while the formulations of Examples 2, 3 and 4 contained ammonium hydroxide, urea and ammonium bicarbonate, respectively, as enhancing agents. The deodorizing characteristics of the respective aerosols are set forth in Table IV:

TABLE IV

EFFECT OF DEODORIZING ENHANCING AGENTS
% Malodor (Propionic Acid) Reduction

| Aerosol Formulation | % Enhancing Agent | 0.5 Minute After Deodorizer Injection | 5.0 Minutes After Deodorizer Injection |
|---|---|---|---|
| Ex. 1 | 0% (none) | 14 | 16 |
| Ex. 2 | 0.5% $NH_4OH$ | 57 | 52 |
| Ex. 3 | 15% urea | 45 | 54 |
| Ex. 4 | 3% $NH_4HCO_3$ | 32 | 31 |

As may be seen from the above data, the addition of the ammonia-producing enhancing agents to the alkaline deodorizing agent provides superior odor reduction.

E.

Criticality Of Droplet Size Of The Deodorizers of the Invention

Residues left by sample deodorizers of the invention were compared with residues produced employing identical aerosol formulations but having larger droplet sizes. Thus, the formulation of Example 3 was compared with aerosol formulations (Controls D–G) having identical chemical compositions but in which the deodorizer solution was aerosolized with average droplet sizes varying from 52 microns (Control D) to 75 microns (Control G) by weight. Both Example 2 and Controls D–G were prepared by dispersing the deodorizer solution in a hydrocarbon propellant (in 65:35 proportion by weight).

Similarly, the residues left by aerosols having the composition of Example 5 but differing in droplet sizes from 35 microns (Example 4A) to 46 microns (Example 4F), and upwards from 52 microns (Control H) to 73 microns (Control K) were compared. To complete the comparison, the residue left by a dry powder aerosol (Control L) was also determined. The dry powder aerosol contained 2% micronized sodium bicarbonate, 0.35% "Cabosil" fumed silica, 14% ethanol, and 84% of a hydrocarbon propellant (70 psig). The visibility of the residues formed by the respective test aerosols was evaluated by a "Dusting Test Method". The method involved placing two black surfaces, one having a matter finish, and the other having a glossy finish, in an unventilated room having a volume of approximately 800 cu. ft. (10 ft.×10 ft.×8 ft.). One half of each of the clean surfaces was covered with paper. The deodorizing solution being tested was sprayed throughout the room for two seconds. The spray was allowed to settle for two hours. The spraying procedure was then repeated 10 times.

After each spray application the paper was removed and the clean surface and exposed surface were compared to identify any visible residue. The unexposed surface was recovered before the next spray cycle.

A product was deemed unacceptable with regard to dusting if a residue was visible before the tenth spray. A product was deemed borderline acceptable if a residue was barely visible after the 10th spray. A product was deemed acceptable if absolutely no residue was visible after the 10th spray.

The residues left after application of the aerosols of Example 3 and Controls D–G are indicated in Table V below; the residues left by the aerosols of Examples 5A–5F and Controls H-L are identified in Table VI below:

TABLE V

AEROSOL DROPLET SIZE VS. VISIBLE RESIDUE

|  | Ex 3 | Controls D | E | F | G |
|---|---|---|---|---|---|
| Average Droplet Size (By Wt.) | 36 u | 52 u | 65 u | 68 u | 75 u |
| >60 u (Wt. %) | 13% | 35% | 48% | 54% | 69% |
| >80 u (Wt. %) | 3% | 17% | 30% | 34% | 42% |
| >100 u (Wt. %) | 0.5% | 7% | 18% | 19% | 19% |
| % of droplets <10 u (by count) | 99.7% | 99.6% | 99.8% | 99.4% | 79.9% |
| % of droplets <1 u (by count) | 94.6% | 93.6 | 94.5 | 92.1 | 50.5% |
| Visible Residue (By Dusting Test Method) | No | Yes | Yes | Yes | Yes |

TABLE VI

AEROSOL DROPLET SIZE VS. VISIBLE RESIDUE

|  | Ex. 5A | Ex. 5B | Ex. 5C | Ex. 5D | Ex. 5E | Ex. 5F |
|---|---|---|---|---|---|---|
| Average Droplet Size (By Wt.) | 35μ | 40μ | 44μ | 46μ | 45μ | 46μ |
| >60 u (Wt. %) | 17% | 14% | 24% | 27% | 12% | 4% |
| >80 u (Wt. %) | 8% | 2% | 9% | 12% | 12% | 11% |
| >100 u (Wt. %) | 4% | 0.5% | 2% | 4% | 5% | 4% |
| % of droplets <10 u (by count) | 99.9% | 97.8% | 99.5% | 99.8% | 99.9% | 99.7% |
| % of droplets <1 u (by count) | 98.1% | 83.8% | 92.2% | 94.7% | 95.7% | 93.6% |
| Visible Residue (By Dusting Test Method) | No | No | No | Very slight, borderline acceptable | | |

TABLE VI-continued
AEROSOL DROPLET SIZE VS. VISIBLE RESIDUE

| | Controls | | | | |
|---|---|---|---|---|---|
| | H | I | J | K | L |
| Average Droplet Size (By Wt.) | 52μ | 57μ | 67μ | 73μ | 16μ |
| >60 u (Wt. %) | 36% | 42% | 51% | 57% | 0% |
| >80 u (Wt. %) | 17% | 19% | 33% | 38% | 0% |
| >100 u (Wt. %) | 7% | 6% | 19% | 24% | 0% |
| % of droplets <10 u (by count) | 99.5% | 97.5% | 99.6% | 99.6% | 48.4% |
| % of droplets <1 u (by count( | 92.2% | 83.1% | 93.5% | 93.5% | 0% |
| Visible Residue (By Dusting Test Method) | Yes | Yes | Yes | Yes | Yes |

F.

Additional Aerosol Formulations Of The Invention

Examples 11-17 below illustrate additional deodorizer solution formulations which form aerosols within the scope of the present invention:

| | Wt. % |
|---|---|
| EXAMPLE 11 | |
| Dipotassium citrate | 10.0 |
| Fragrance | 1.0 |
| Water | 89.0 |
| | 100.0 |
| EXAMPLE 12 | |
| Sodium dihydrogen phosphate | 8.0 |
| Ammonium hydroxide (28%) | 0.5 |
| Fragrance | 1.0 |
| Water | 90.5 |
| | 100.0 |
| EXAMPLE 13 | |
| Potassium tetraborate | 5.0 |
| Potassium bicarbonate | 3.0 |
| Urea | 8.0 |
| Fragrance | 1.0 |
| Water | 83.0 |
| | 100.0 |
| EXAMPLE 14 | |
| Calcium propionate | 10.0 |
| Fragrance | 0.5 |
| Water | 89.5 |
| | 100.0 |
| EXAMPLE 15 | |
| Potassium bicarbonate | 10.0 |
| Potassium pyrophosphate | 1.2 |
| Fragrance | 0.8 |
| Water | 88.0 |
| | 100.0 |
| EXAMPLE 16 | |
| Potassium bicarbonate | 8.0 |
| Magnesium chloride | 4.0 |
| Urea | 5.0 |
| Fragrance | 1.0 |
| Water | 82.0 |
| | 100.0 |
| EXAMPLE 17 | |
| Zinc Acetate | 5.0 |
| Urea | 15.0 |
| Fragrance | 1.0 |
| Water | 79.0 |
| | 100.0 |

The preceding examples are intended to illustrate but not limit the air deodorizer composition and method of the present invention. It will be understood that the scope of the invention is rather defined by the claims appended hereto.

What is claimed is:

1. An air deodorizer comprising an aerosol of finely divided liquid droplets in air, the droplets comprising a solution containing from 2-25% by weight of a non-toxic, non-oxidizing, deodorizing agent which reacts with malodors in the air, in a solvent selected from the group consisting of water and aqueous mixtures with lower alkanols and other non-toxic volatile solvents, said solution having a pH between 4 and 10, and said droplets having a weight average droplet size of less than 50 microns, more than 90% of said droplets having a size, by count, of less than 10 microns; said aerosol, upon deposition, normally forming virtually no visible residue on furniture or other surfaces within a room or other volume treated therewith.

2. The air deodorizer of claim 1, wherein no more than 30% by weight of the liquid droplets has a droplet size larger than 60 microns; no more than 15% by weight of the liquid droplets has a droplet size larger than 80 microns; no more than 6% by weight of the liquid droplets has a droplet size larger than 100 microns; and more than 75% of said droplets in fact has a droplet size, by count, of less than 1 micron.

3. The air deodorizer of claim 1, wherein the air deodorizing agent is selected from the group consisting of the normally solid alkali metal bicarbonates, carbonates and borates; the mono-, di- and tri-alkali metal ortho-phosphates; the alkali metal tripolyphosphates, pyrophosphates and hexametaphosphates; the alkali metal salts of carboxylic acids; and mixtures thereof.

4. The air deodorizer of claim 1, wherein the air deodorizing agent is sodium or potassium bicarbonate, or a mixture thereof.

5. An air deodorizer comprising an aerosol of finely divided liquid droplets in air, the droplets comprising a solution containing from 2-25% by weight of a non-toxic, non-oxidizing alkaline deodorizing agent which reacts with malodors in the air, in a solvent selected from the group consisting of water and aqueous mixtures with lower alkanols and other non-toxic volatile solvents, and up to 20% by weight of a deodorizing enhancing agent which releases ammonia into the atmosphere under normal ambient conditions, said solution having a pH between 4 and 10, and said droplets having a weight average droplet size of less than 50 microns, more than 90% of said droplets having a size, by count, of less than 10 microns; said aerosol, upon deposition, normally forming virtually no visible residue on furniture or other surfaces within a room or other volume treated therewith.

6. The air deodorizer of claim 5, wherein the deodorizing enhancing agent is present in the solution in an amount sufficient to release ammonia into the solution in the proportion of from 0.05 to 0.5% by weight thereof.

7. The air deodorizer of claim 5, wherein no more than 30% by weight of the liquid droplets has a droplet size larger than 60 microns; no more than 15% by weight of the liquid droplets has a droplet size larger than 80 microns; no more than 6% by weight of the liquid droplets has a droplet size larger than 100 microns; and more than 75% of said droplets in fact has a droplet size, by count, of less than 1 micron.

8. A method for deodorizing air, which comprises dispensing the aerosol of claim 5 into the air.

* * * * *